(12) United States Patent
Bode

(10) Patent No.: US 10,702,660 B2
(45) Date of Patent: Jul. 7, 2020

(54) ASSEMBLY FOR A DRUG DELIVERY DEVICE

(71) Applicant: SANOFI-AVENTIS DEUTSCHLAND GMBH, Frankfurt am Main (DE)

(72) Inventor: Andreas Bode, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 292 days.

(21) Appl. No.: 15/544,181

(22) PCT Filed: Jan. 19, 2016

(86) PCT No.: PCT/EP2016/050989
§ 371 (c)(1),
(2) Date: Jul. 17, 2017

(87) PCT Pub. No.: WO2016/116432
PCT Pub. Date: Jul. 28, 2016

(65) Prior Publication Data
US 2018/0008783 A1  Jan. 11, 2018

(30) Foreign Application Priority Data

Jan. 19, 2015 (EP) .................................... 15151571

(51) Int. Cl.
*A61M 5/315* (2006.01)
(52) U.S. Cl.
CPC ...... *A61M 5/31551* (2013.01); *A61M 5/3156* (2013.01); *A61M 5/31541* (2013.01);
(Continued)
(58) Field of Classification Search
CPC .......... A61M 5/31551; A61M 5/31541; A61M 5/3156; A61M 5/31585; A61M 2205/581; A61M 2205/582
See application file for complete search history.

(56) References Cited

U.S. PATENT DOCUMENTS

| 2005/0033244 A1* | 2/2005 | Veasey ................... A61M 5/24 604/211 |
| 2010/0200787 A1 | 8/2010 | Hirschel et al. |
| 2012/0172814 A1* | 7/2012 | Plumptre .......... A61M 5/31543 604/207 |

FOREIGN PATENT DOCUMENTS

| CN | 1780652 | 5/2006 |
| CN | 102209563 | 10/2011 |

(Continued)

OTHER PUBLICATIONS

International Search Report and Written Opinion in International Application No. PCT/EP2016/050989, dated Mar. 30, 2016, 13 pages.

(Continued)

*Primary Examiner* — Kami A Bosworth
*Assistant Examiner* — Leah J Swanson
(74) *Attorney, Agent, or Firm* — Fish & Richardson P.C.

(57) ABSTRACT

An assembly includes a clutch member and a drive member movable relative to one another between a first relative position and a second relative position, in the first relative position, the clutch member and/or the drive member is rotatable relative to a housing, in the second relative position, the deflectable feature is arranged to prevent rotation of the clutch member and/or of the drive member relative to the housing, and wherein the deflectable feature and the interaction feature are arranged such that, when the clutch member and the drive member are moved relative to one another from the first relative position into the second relative position, the deflectable feature and the interaction feature mechanically interact in order to deflect the deflectable feature.

19 Claims, 9 Drawing Sheets

(52) U.S. Cl.
CPC ..... *A61M 5/31585* (2013.01); *A61M 5/31575* (2013.01); *A61M 2205/581* (2013.01); *A61M 2205/582* (2013.01)

(56) References Cited

FOREIGN PATENT DOCUMENTS

| | | |
|---|---|---|
| CN | 102448526 | 5/2012 |
| EP | 2208503 | 7/2010 |
| JP | 2012-528625 | 11/2012 |
| JP | 2013-512070 | 4/2013 |
| WO | WO 2004/078239 | 9/2004 |
| WO | WO 2010/139632 | 12/2010 |
| WO | WO 2011/060785 | 5/2011 |
| WO | WO 2013/081539 | 6/2013 |

OTHER PUBLICATIONS

International Preliminary Report on Patentability in International Application No. PCT/EP2016/050989, dated Jul. 25, 2017, 8 pages.

\* cited by examiner

ASSEMBLY FOR A DRUG DELIVERY DEVICE

CROSS REFERENCE TO RELATED APPLICATIONS

This application is a U.S. national stage application under 35 USC § 371 of International Application No. PCT/EP2016/050989, filed on Jan. 19, 2016, which claims priority to European Patent Application No. 15151571.5, filed on Jan. 19, 2015, the entire contents of which are incorporated herein by reference.

TECHNICAL FIELD

The present disclosure relates to an assembly for a drug delivery device. It also relates to a drug delivery device comprising the assembly.

BACKGROUND

Drug delivery devices, especially devices which are designed for self-administration of medicament or drug by a patient, usually have sophisticated internal mechanisms which are provided to permit setting of a dose of drug to be delivered and dispensing of the dose, for example by transferring a force from a dose button which is pressed by the user to a piston or bung within a cartridge which contains the medicament, thereby displacing the piston with respect to the inner walls of the cartridge in order to expel drug from an outlet of the cartridge.

Often, clutch mechanisms are utilized within these devices in order to couple certain elements of these devices to one another only selectively. One of these devices is disclosed in WO 2004/078239 A1. The drug delivery device utilizes a clutch which cooperates with a clicker and also has a member for resetting the clutch following dispense.

SUMMARY

An advantage of the present disclosure may be to provide a novel and improved assembly, for a drug delivery device. Particularly, an assembly may be provided which facilitates keeping the manufacturing costs low and/or which facilitates a reduction in the part count of the parts required to manufacture the drug delivery device.

An aspect of the present disclosure relates to an assembly for a drug delivery device. Another aspect relates to a drug delivery device comprising the assembly. Features described herein above and below with respect to the assembly do therefore also apply for the drug delivery device and vice versa. In addition to the assembly the drug delivery device preferably comprises a reservoir which holds drug or medicament, such as a cartridge, for example.

The drug delivery device may be a user-operable drug delivery device. The drug delivery device may be a variable dose device where the size of the dose to be delivered by the drug delivery device may be varied by the user. For example, for setting the size of the dose to be delivered a dose setting action may be performed by the user which allows the dose to be delivered to be increased in multiples of a dosage increment which may be defined by the design of the drug delivery device. The drug delivery device is preferably a disposable delivery device where a reduced part count and cost-effective manufacturing are particularly advantageous. The drug delivery device may be an injection device, such as a needle-based device or a needle-free device. The drug delivery device may be a pen-type device, such as a pen-type injector.

The proposed assembly may be or may comprise a clutch and/or feedback assembly such that the components of the assembly may provide a clutch and/or feedback functionality. The clutch functionality may be a functionality which couples components selectively with each other such that they are movable differently with respect to one other in two different states or positions of the clutch mechanism, for example during dose setting and dose dispense. The feedback functionality may provide an audible and/or tactile feedback such as a clicking noise, for example during an operation of the assembly, such as during dose setting. Accordingly, the feedback functionality may be a clicker functionality.

In an embodiment, the assembly comprises a housing. The housing may house further components of the assembly and/or the device such as a clutch member, a drive member, a piston rod and/or a dose setting member. The housing may have a proximal end and a distal end.

The "distal end" of the housing or a component of the assembly is that end which is arranged or is to be arranged closest to the dispensing end of the drug delivery device, i.e. that end from which drug is expelled from the device. The "proximal end" of the housing or a component of the assembly is that end which is, or is to be, arranged furthest away from the dispensing end of the drug delivery device. A "distal direction" as referred herein may be a direction towards the dispensing end. A "proximal direction" as referred to herein may be a direction away from the dispensing end. The respective direction may be an axial direction.

In an embodiment, the assembly comprises a drive member. The drive member may be provided to drive a piston rod. For example, the drive member may be engaged with the piston rod. The drive member may be a drive sleeve.

In an embodiment, the assembly comprises a clutch member. The clutch member may be provided to achieve a selective coupling of the drive member with respect to the housing, for example rotatable with respect to the housing in a first state and rotationally locked with respect to the housing in a second state. The clutch member may be a clutch sleeve. The drive member may be received in the clutch sleeve.

In an embodiment, one of the clutch member and the drive member is provided with at least one deflectable feature. The clutch member or the drive member may be provided with the deflectable feature. The deflectable feature may be a finger. The deflectable feature may extend in the axial direction, particularly in an undeflected state. The deflectable feature may be radially deflectable, preferably by means of mechanical cooperation with an interaction feature. The deflectable feature is preferably rigidly connected or integrally formed with the drive member or the clutch member. The deflectable feature may be unitarily formed with the respective member. The deflectable feature may be deflectable with respect to a body of the clutch member or the drive member, particularly in the radial and/or outward direction. The deflectable feature may be arranged to be deflected towards the housing.

In an embodiment, the other one of the clutch member and the drive member, i.e. the one which is not provided with the at least one deflectable feature, is provided with at least one interaction feature. The interaction feature may extend in the axial direction, preferably towards the deflectable feature. If the interaction feature is provided on the drive member, the interaction feature preferably extends in the proximal direction. If the interaction feature is provided on the clutch member, the interaction feature preferably extends in the distal direction. The interaction feature may be rigid, particularly as compared to the deflectable feature and/or overall. The interaction feature is preferably rigidly connected or integrally formed with the drive member or the clutch member respectively. The interaction feature may be unitarily formed with the respective member. The interaction feature may be arranged and configured to mechanically cooperate with the at least one deflectable feature of the clutch member, for example to selectively couple the clutch member and/or the drive member to a further component of the assembly, e.g. by deflecting the deflectable feature, such as in the radial direction, from a first position, e.g. an undeflected position, to a second position, e.g. a deflected position.

As compared to prior art devices, the drive member may thus provide at least two functionalities, such as driving the piston rod and also having a feature which cooperates with a feature of the clutch member to provide a clutch functionality as detailed above and also below.

In an embodiment, the clutch member and the drive member are movable relative to one another between a first relative position and a second relative position. The first relative position and the second relative position may be axially offset with respect to each other. Accordingly the relative movement may be a relative axial movement with or without relative rotation between the clutch member and the drive member. For example, the clutch member may be movable with respect to the drive member from a first position to a second position where the first position is the first relative position and the second position is the second relative position. The drive member may be stationary during this movement or at least move less than the clutch member. Relative movement between clutch member and drive member from the first relative position to the second relative position may be a distal movement. The movement from the first relative position to the second relative position may be reversible, such that when the components are in the second relative position they may be moved back into the first relative position.

In the first relative position, the clutch member and/or the drive member is preferably rotatable relative to the housing. In this position, there may be no interaction between the deflectable feature and the housing, e.g. on account of the deflectable feature being not deflected.

In the second relative position, the deflectable feature may be arranged to prevent and preferably prevents rotation of the clutch member and/or of the drive member relative to the housing, for example by mechanical cooperation of the deflectable feature with the housing. Particularly, in the second relative position the deflectable feature may establish a coupling between clutch member and housing to prevent relative rotation between clutch member and housing. For doing so, the deflectable feature, in the second relative position, may engage a spline feature provided on the housing which prevents relative rotation of the clutch member and/or the drive member relative to the housing.

The deflectable feature and the interaction feature may be arranged such that when the clutch member and the drive member are moved relative to one another from the first relative position into the second relative position, the deflectable feature and the interaction feature mechanically interact in order to deflect the deflectable feature, particularly in the radial and/or outward direction and preferably towards an inner surface of the housing. Thus, in the second relative position, of drive member and clutch member, the deflectable feature may be deflected, particularly as compared to the first relative position. Preferably, the deflectable feature is deflected more in the outward direction in the second relative position than in the first relative position.

Thus, the relative movement between clutch member and drive member may be utilized to move the deflectable feature and, in turn, to establish a selective coupling of drive member and/or clutch member relative to the housing. The selective coupling may be released when the clutch member and the drive member are moved back into the first relative position. As compared to prior art devices, features of the drive member and the clutch member interact and move the deflectable feature in order to establish a coupling between drive member and/or clutch member and housing. No separate member is required to provide the clutch functionality. Accordingly, the proposed clutch mechanism is highly integrated and has a low number of parts as the drive member is usually present in a drug delivery device anyway to drive the piston rod.

In an embodiment, the deflectable feature and the interaction feature abut in the second relative position and in the first relative position.

In an embodiment, the drive member and/or the clutch member is rotatable relative to the housing in a dose setting and/or dose cancelling mode of the assembly. The drive member and/or the clutch member may be rotatable in a first direction with respect to the housing during setting of a dose and in a second direction with respect to the housing during cancelling or reducing the dose where the second direction is opposite to the first direction. During dose dispense, the drive member and/or the clutch member is preferably not rotatable with respect to the housing. In the first relative position of the clutch member and the drive member, the assembly may be in the dose setting and/or dose cancelling mode of operation, whereas in the second relative position of the clutch member and the drive member the assembly may be in the dose dispensing mode of operation.

In an embodiment, the clutch member is splined to the drive member, preferably permanently splined to the drive member. Accordingly, clutch member and drive member co-rotate with relative axial moment between drive member and clutch member being allowed. Relative rotational movement between drive member and clutch member is preferably prevented. During dose setting, the drive member may move proximally with respect to the clutch member whereas during dose dispense and/or during cancelling or reducing the dose the drive member may move distally with respect to the clutch member. During dose setting and/or dose cancelling, the drive member preferably rotates, whereas there is preferably no relative rotation between drive member and housing on account of the coupling to the housing by the deflectable feature during dose dispense.

In an embodiment, the deflectable feature is an elastically deflectable feature. Accordingly, once deflected, the deflectable feature exerts an elastic restoring force. The elastic restoring force may tend to move the deflectable feature back into the undeflected position. The deflectable feature may be inherently resilient or resiliently mounted or otherwise coupled to the remainder of the respective member such as to a clutch member body or a drive member body. The deflectable feature may be a resilient finger such as resilient axial finger. During deflection it may be radially and/or outwardly deflected. The restoring force may act in the direction opposite to the deflection direction.

In an embodiment, in the second relative position, the deflected deflectable feature provides a force, e.g an axially directed force, which tends to establish the first relative position between the clutch member and the drive member. Particularly, the restoring force of the elastically deflected deflectable feature which is arranged to prevent rotation of the clutch member and/or the drive member relative to the housing may be used to provide the force to move the clutch member and the drive member from the second relative position into the first relative position. Accordingly by means of the restoring force, when in the second relative position, the clutch member may be moved, particularly in an axial direction, e.g. in the proximal direction, relative to the drive member such that the drive member and the clutch member assume the first relative position.

As the deflectable feature couples to the housing and simultaneously provides the restoring force which is used to decouple the drive member and/or the clutch member from the housing, a separate spring member as in prior art devices may be dispensed with.

In an embodiment, the at least one interaction feature comprises an oblique surface. The oblique surface may be arranged to deflect the deflectable feature in the radial direction, when the deflectable feature contacts the oblique surface and when the clutch member and the drive member are moved relative to one another, particularly in the axial direction, from the first relative position into the second relative position. The deflectable feature and the interaction feature may of course follow the relative movement of the drive member and the clutch member, with the deflectable feature being, in addition, deflected during this relative movement.

In an embodiment, the at least one deflectable feature is integrally formed within the clutch member. That is to say, the clutch member, including a clutch member body and the deflectable feature may be an integral part or a unitary part. In an embodiment, the at least one interaction feature is integrally formed within the drive member. Accordingly the drive member, including a drive member body and the interaction feature, may be a unitary part or an integral part.

Accordingly, separate members for providing the interaction feature and/or the deflectable feature can be dispensed with.

In an embodiment, the at least one deflectable feature is an axially oriented finger which is arranged to be deflected radially.

In an embodiment, the assembly comprises a plurality of deflectable features. The deflectable features may be distributed evenly in the circumferential direction. Consequently, the distances between two arbitrary adjacent deflectable features may be constant.

In an embodiment, the assembly comprises a plurality of interaction features. One interaction feature may be arranged to interact with one deflectable feature, preferably with only one of the plurality of deflectable features, in order to deflect the deflectable feature.

In an embodiment, one interaction feature may be arranged to cooperate with a plurality of deflectable features in order to deflect the deflectable features.

In an embodiment, the clutch member comprises a clutch feature. The clutch feature may be provided in addition to the deflectable feature. The clutch feature may be designed to mechanically interact with a movable member of the assembly, which is expediently different from the drive member. The clutch feature may be designed to releasably couple the clutch member and the movable member, e.g. rotationally, particularly when the drive member and the clutch member are in the first relative position. In the second relative position of drive member and clutch member, the movable member and the clutch member may be decoupled such that relative rotation is allowed. Accordingly, the clutch member may comprise the deflectable feature as well as the clutch feature and provide a selective coupling to the housing in the second relative position and to the further movable member in the first relative position.

In an embodiment, the assembly comprises a dose setting member. The dose setting member may be manipulated by a user for setting and/or cancelling a dose. For example, the dose setting member is rotatable in a first direction relative to the housing for setting a dose and/or rotatable in a second direction relative to the housing which is opposite to the first direction for cancelling or reducing the set dose. In the first relative position, the clutch member and/or the drive member may be rotationally locked with respect to the dose setting member. In the second relative position relative rotation between the dose setting member and the clutch member and/or between the dose setting member and the drive member may be allowed. The dose setting member may be a dose dial member such as a dose dial sleeve. The dose setting member may be the movable member described further above. Accordingly, the clutch feature may establish a selective coupling between the clutch member and the dose setting member.

In an embodiment, the assembly comprises a button. The button may be operated by the user to switch the assembly from the dose setting and/or dose cancelling mode of operation into the dose dispensing mode of operation. When pressing the button, the clutch member and the drive member may be moved from the first relative position into the second relative position, e.g. by the force exerted by the user. When the force is released, the clutch member and the drive member may assume the first relative position.

In an embodiment, the assembly comprises a piston rod. The drive member may be arranged to mechanically interact with the piston rod to drive the piston rod relative to the housing, particularly in the distal direction. The drive member may be arranged to drive the piston rod when the drive member is displaced in the distal direction relative to the housing. For example, the drive member may be engaged with the piston rod.

In an embodiment, the interaction feature is arranged on a protruding portion, such as a radially protruding portion, of the drive member or the clutch member. The interaction feature may be oriented axially, particularly in the proximal direction. The protruding portion may be circumferentially disposed. The protruding portion may be a flange. The interaction feature may itself protrude from the protruding portion, for example axially. The interaction feature may be offset or spaced apart from a drive member body or a clutch member body in the radial direction.

In an embodiment, the drive member or the clutch member is provided with one or a plurality of feedback features. The feedback features may be an integral part of the drive member or the clutch member. The feedback features may be designed to generate an audible and/or tactile feedback when the drive member and/or the clutch member rotates relative to the housing. The feedback features may be designed to releaseably mechanically engage corresponding features in the housing to generate the audible and/or tactile feedback. The feedback features may be provided on the same one of the drive member and the clutch member on which the interaction feature is provided, e.g. on the drive member.

In an embodiment, the feedback features are axially, particularly distally, offset from the interaction feature and, preferably, from the protruding portion. Between the feedback features and the interaction feature, an interspace may be formed. For example, a thread such as a thread for a last dose nut, may be provided between the interaction feature and the feedback features. The feedback features may be arranged circumferentially. The feedback features may be provided around a flange of the drive member or the clutch member.

The respective feedback feature may comprise a flexible finger such that the assembly comprises a plurality of flexible fingers. The respective finger may be flexed when engaging or disengaging the corresponding feature on the housing. The respective flexible finger may be oriented in an azimuthal direction. Accordingly, the respective flexible finger may extend in a circumferential direction.

In an embodiment, the corresponding features comprise at least one feature which is engaged by the deflectable feature to form a splined connection between the deflectable feature and the housing in the second relative position of clutch member and drive member. Consequently, the same features can be used for the splined connection between deflectable feature and housing and for providing feedback in cooperation with the feedback features.

The surfaces of the feedback features which engage the corresponding features to provide the feedback may be rounded, particularly such that no splined connection is established between the corresponding features and the feedback features which would prevent relative movement between the feedback features and the corresponding features. The surfaces of the deflectable feature and the corresponding feature which engage for the splined connection may be plane and abut so as to prevent relative rotation between the deflectable feature and the housing in the second relative position.

In an embodiment, the corresponding features are evenly distributed in the circumferential direction. Thus, the distances between arbitrary adjacent corresponding features may be constant.

In an embodiment, the feedback features are unevenly distributed in the circumferential direction. Consequently, the distances in the circumferential direction between adjacent feedback features may vary. The feedback features may be distributed in the circumferential direction such that, for each relative position between the member on which the feedback features are provided and the housing, for example for each increment of the settable dose, a plurality of feedback features is engaged with a corresponding feature. Accordingly, it is guaranteed that feedback is generated for each dosage increment.

In an embodiment, the feedback features are arranged so as to guarantee that at every relative position, particularly every possible azimuthal position corresponding to one dosage increment, between the feedback features and the corresponding features a plurality of feedback features are engaged with a plurality of corresponding features. Also, at least one or more than one feedback feature is preferably not engaged with one corresponding feature. Thereby, it can be guaranteed that proper feedback is provided in every possible relative position between the feedback features and the corresponding features.

In an embodiment, one, an arbitrary number of two or more of the following components or features is a plastic component or feature: housing, clutch member, deflectable feature, drive member, interaction feature, feedback feature, piston rod, button, and dose setting member. Particularly, all of the recited components or features may be plastic components or features. As the deflectable feature can be integrated in a plastic part, a separate spring for providing a restoring force for decoupling the deflectable feature with respect to the housing and/or for establishing the first relative position between clutch member and drive member may be dispensed with and manufacturing costs are kept low.

According to one embodiment at least one of the clutch member, the deflectable feature, the drive member and the interaction feature comprises a biodegradable matter, preferably a biodegradable plastic material.

A particularly advantageous embodiment of an assembly according to the present disclosure comprises:
a housing;
a clutch member; and
a drive member, wherein
one of the clutch member and the drive member is provided with at least one deflectable feature and the other one of the clutch member and the drive member is provided with at least one interaction feature,
the clutch member and the drive member are movable relative to one another between a first relative position and a second relative position,
in the first relative position, the clutch member and/or the drive member is rotatable relative to the housing,
in the second relative position, the deflectable feature is arranged to prevent rotation of the clutch member and/or of the drive member relative to the housing, and
the deflectable feature and the interaction feature are arranged such that, when the clutch member and the drive member are moved relative to one another from the first relative position into the second relative position, the deflectable feature and the interaction feature mechanically interact in order to deflect the deflectable feature.

Some advantages associated with this assembly have already been described above.

The features disclosed in conjunction with different embodiments may, of course, be combined with one another, if they are not contradictory.

Further features, expediencies and advantageous embodiments will become readily apparent from the following description of the exemplary embodiments in conjunction with the drawings.

DETAILED DESCRIPTION

Figure 1:
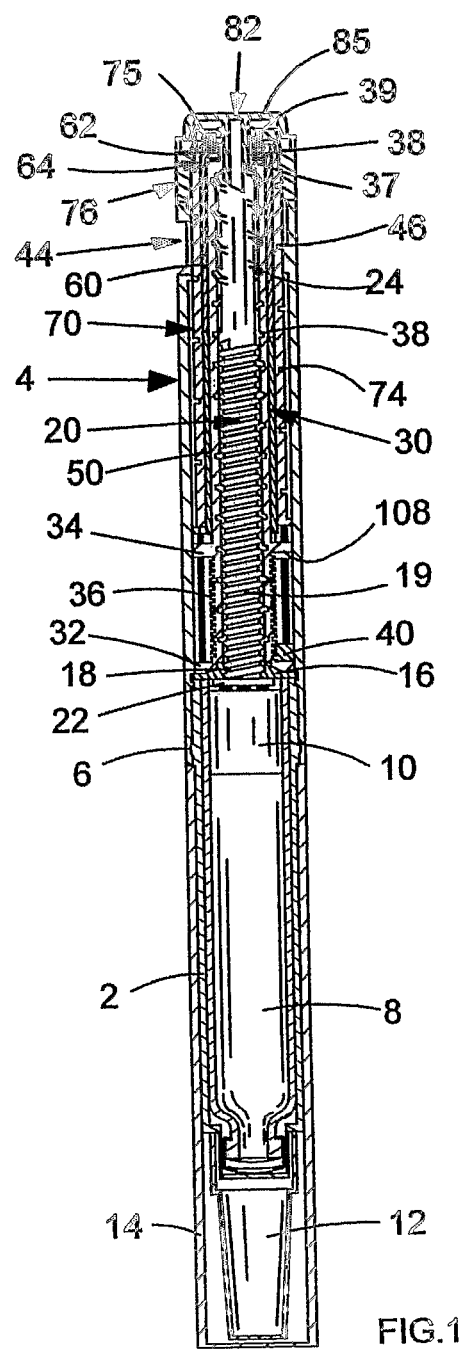
FIG. 1 shows a sectional view of a first embodiment of a drug delivery device in a first, cartridge full, position.
Figure 2:
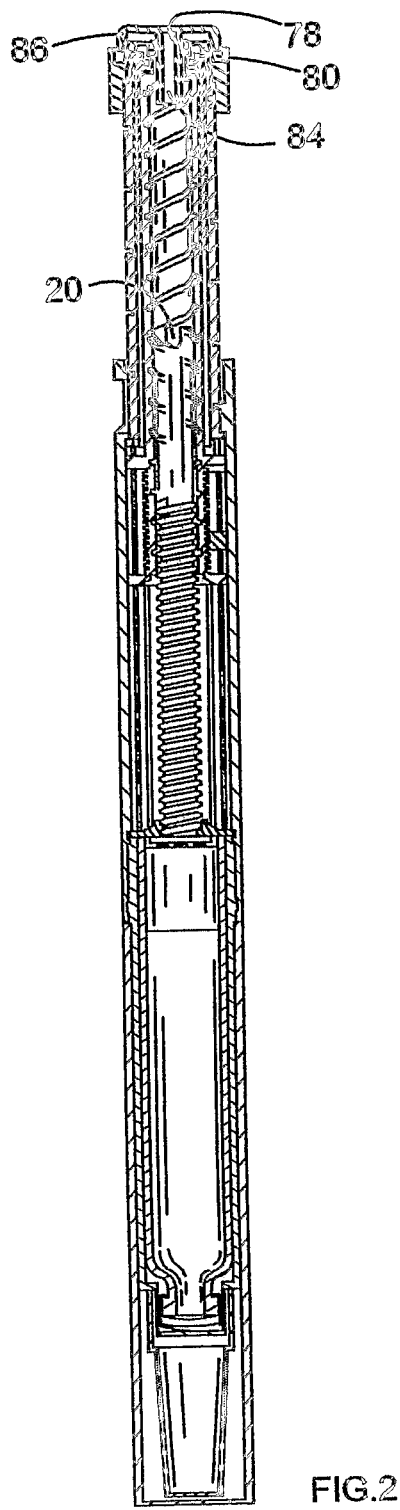
FIG. 2 shows a sectional view of the drug delivery device of FIG. 1 in a second, maximum first dose dialed, position.
Figures 3, 4:
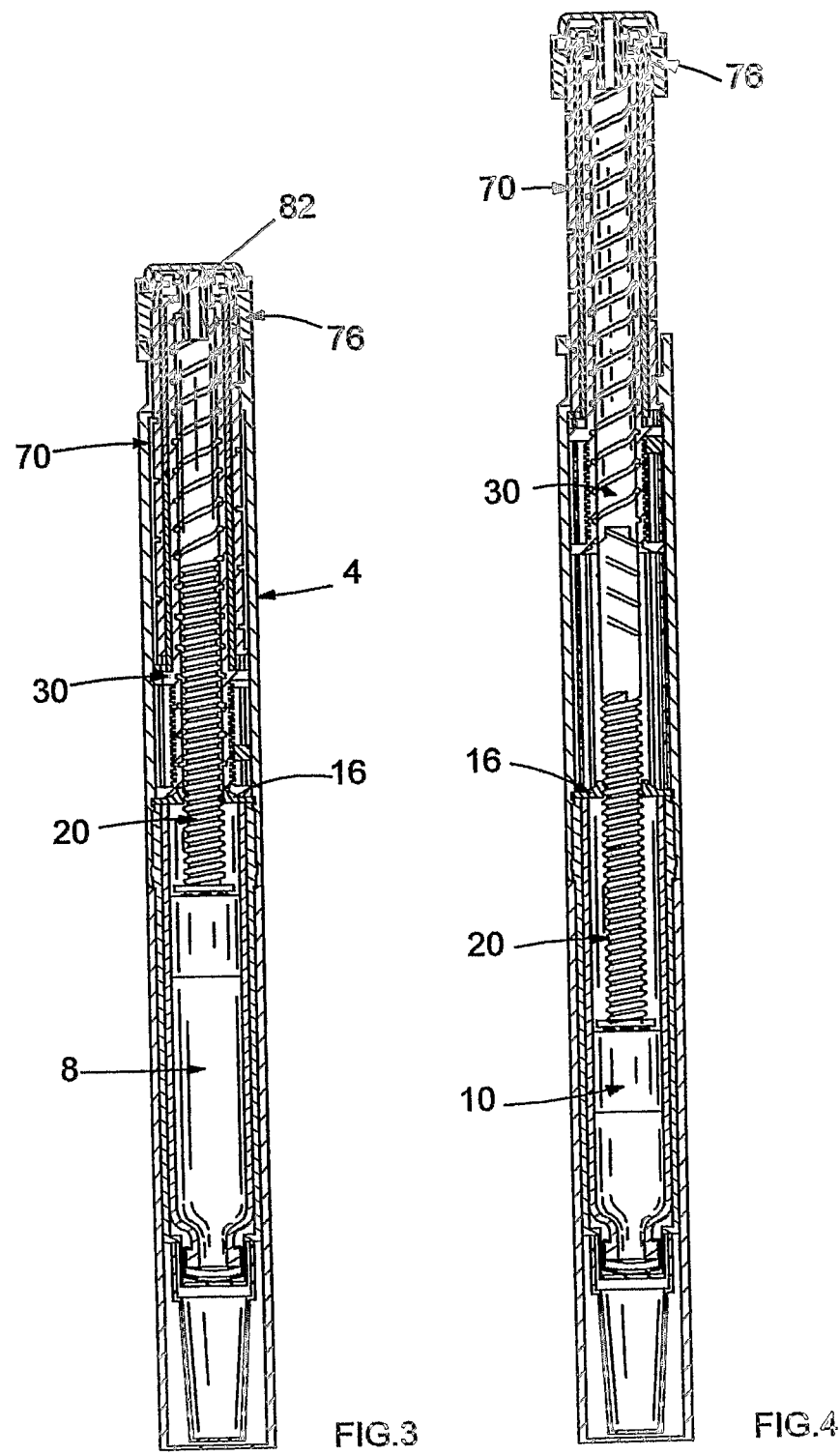
FIG. 3 shows a sectional view of the drug delivery device of FIG. 1 in a third, maximum first dose dispensed, position.
FIG. 4 shows a sectional view of the drug delivery device of FIG. 1 in a fourth, final dose dialed, position.
Figure 5:
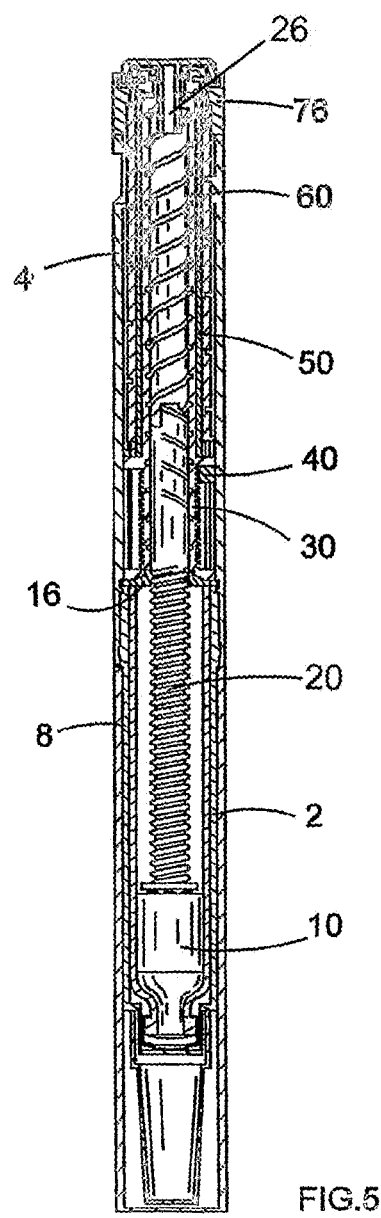
FIG. 5 shows a sectional view of the drug delivery device of FIG. 1 in a fifth, final dose dispensed, position.

Referring first to FIGS. 1 to 5, there is shown a drug delivery device in a number of positions.

The drug delivery device comprises a housing having a first cartridge retaining part 2, and second main (exterior) housing part 4. A first end of the cartridge retaining means 2 and a second end of the main housing 4 are secured together by retaining features 6. In the illustrated embodiment, the cartridge retaining means 2 is secured within the second end of the main housing 4.

A cartridge 8 from which a number of doses of a medicinal product, like a drug or a medicament, may be dispensed is provided in the cartridge retaining part 2. A piston 10 is retained in a first end of the cartridge 8.

The term "drug" or "medicament", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36[Asp28] Exendin-4(1-39)-Lys6-NH2,
des Asp28 Pro36, Pro37, Pro38Exendin-4(1-39)-NH2,
H-(Lys)6-des Pro36, Pro38[Asp28] Exendin-4(1-39)-NH2,
H-Asn-(Glu)5des Pro36, Pro37, Pro38[Asp28] Exendin-4(1-39)-NH2,
des Pro36, Pro37, Pro38[Asp28] Exendin-4(1-39)-(Lys)6-NH2, H-(Lys)6-des Pro36, Pro37, Pro38[Asp28] Exendin-4(1-39)-(Lys)6-NH2, H-Asn-(Glu)5-des Pro36, Pro37, Pro38[Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38[Trp(O2)25] Exendin-4(1-39)-NH2, H-(Lys)6-des Pro36, Pro37, Pro38[Trp(O2)25, Asp28] Exendin-4(1-39)-NH2, H-Asn-(Glu)5-des Pro36, Pro37, Pro38[Trp(O2)25, Asp28] Exendin-4(1-39)-NH2, des Pro36, Pro37, Pro38[Trp(O2)25, Asp28] Exendin-4(1-39)-(Lys)6-NH2, H-(Lys)6-des Pro36, Pro37, Pro38[Trp(O2)25, Asp28] Exendin-4(1-39)-(Lys)6-NH2, H-Asn-(Glu)5-des Pro36, Pro37, Pro38[Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38[Met(O)14, Asp28] Exendin-4(1-39)-NH2, H-Asn-(Glu)5-des Pro36, Pro37, Pro38[Met(O)14, Asp28] Exendin-4(1-39)-NH2, des Pro36, Pro37, Pro38[Met(O)14, Asp28] Exendin-4(1-39)-(Lys)6-NH2, H-(Lys)6-des Pro36, Pro37, Pro38[Met(O)14, Asp28] Exendin-4(1-39)-(Lys)6-NH2, H-Asn-(Glu)5 des Pro36, Pro37, Pro38[Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38[Met(O)14, Trp(O2)25] Exendin-4(1-39)-NH2, H-(Lys)6-des Pro36, Pro37, Pro38[Met(O)14, Asp28] Exendin-4(1-39)-NH2, H-Asn-(Glu)5-des Pro36, Pro37, Pro38[Met(O)14, Trp(O2) 25, Asp28] Exendin-4(1-39)-NH2, des Pro36, Pro37, Pro38[Met(O)14, Trp(O2)25, Asp28] Exendin-4(1-39)-(Lys)6-NH2, H-(Lys)6-des Pro36, Pro37, Pro38[Met(O)14, Trp(O2)25, Asp28] Exendin-4(S1-39)-(Lys)6-NH2, H-Asn-(Glu)5-des Pro36, Pro37, Pro38[Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 13 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A removable cap 12 is releasably retained over a second end of the cartridge retaining part 2. In use the removable cap 12 can be replaced by a user with a suitable needle unit (not shown). A replacable cap 14 is used to cover the cartridge retaining part 2 extending from the main housing 4. Preferably, the outer dimensions of the replaceable cap 14 are similar or identical to the outer dimensions of the main housing 4 to provide the impression of a unitary whole when the replaceable cap 14 is in position covering the cartridge retaining part 2.

In the illustrated embodiment, an insert 16 is provided at a first end of the main housing 4. The insert 16 is secured against rotational or longitudinal motion. The insert 16 is provided with a threaded circular opening 18 extending therethrough. Alternatively, the insert may be formed integrally with the main housing 4 having the form of a radially inwardly directed flange having an internal thread.

A first thread 19 extends from a first end of a piston rod 20. The piston rod 20 is of generally circular section. The first end of the piston rod 20 extends through the threaded opening 18 in the insert 16. A pressure foot 22 is located at the first end of the piston rod 20. The pressure foot 22 is disposed to abut a second end of the cartridge piston 10. A second thread 24 extends from a second end of the piston rod 20. In the illustrated embodiment the second thread 24 comprises a series of part threads rather than a complete thread. The illustrated embodiment is easier to manufacture and helps to reduce the overall force required for a user to actuate the device when dispensing the medicinal product.

The first thread 19 and the second thread 24 are oppositely disposed. The second end of the piston rod 20 is provided with a receiving recess 26.

A drive sleeve or drive member 30 extends about the piston rod 20. The drive sleeve 30 is generally cylindrical. The drive sleeve 30 is provided at a first end with a first radially extending flange 32. A second radially extending flange 34 is provided spaced a distance along the drive sleeve 30 from the first flange 32. An intermediate thread 36 is provided on an outer part of the drive sleeve 30 extending between the first flange 32 and the second flange 34. A helical groove (thread) 38 extends along the internal surface of the drive sleeve 30. The second thread 24 of the piston rod is adapted to work within the helical groove 38.

A first end of the first flange 32 is adapted to conform to a second side of the insert 16. A nut 40 is located between the drive sleeve 30 and the main housing 2, disposed between the first flange 32 and the second flange 34. In the illustrated embodiment the nut 40 is a half-nut. This assists in the assembly of the device. The nut 40 has an internal thread matching the intermediate thread 36. The outer surface of the nut 40 and an internal surface of the main housing 4 are keyed together by splines 42 (FIGS. 10, 11, 15 and 16) to prevent relative rotation between the nut 40 and the main housing 4, while allowing relative longitudinal movement therebetween.

A shoulder 37 is formed between a second end of the drive sleeve 30 and an extension 38 provided at the second end of the drive sleeve 30. The extension 38 has reduced inner and outer diameters in comparison to the remainder of the drive sleeve 30. A second end of the extension 38 is provided with a radially outwardly directed flange 39.

A clicker 50 and a clutch or clutch member 60 are disposed about the drive sleeve 30, between the drive sleeve 30 and a dose dial sleeve or dose setting member 70 (described below).

Figure 6:
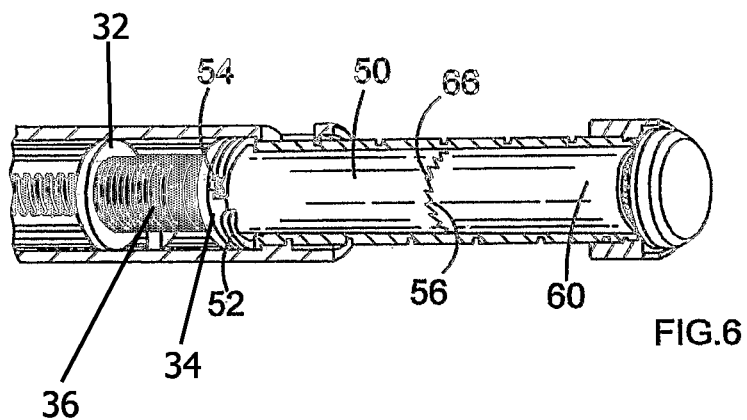
FIG. 6 shows a cut-away view of a first detail of the drug delivery device of FIG. 1.
Figure 7:
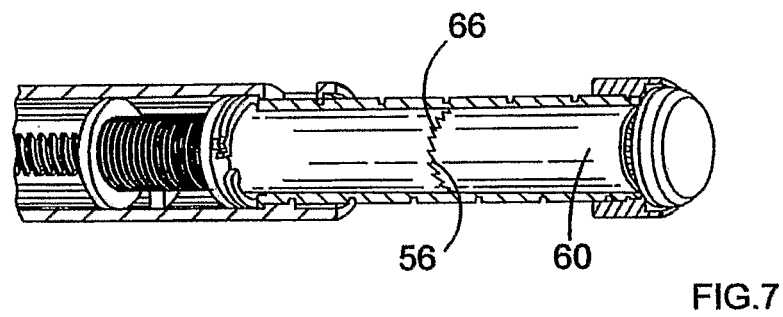
FIG. 7 shows a partially cut-away view of a second detail of the drug delivery device of FIG. 1.

The clicker 50 is located adjacent the second flange 34 of the drive sleeve 30. The clicker 50 is generally cylindrical and is provided at a first end with a flexible helically extending arm 52 (FIG. 6). A free end of the arm 52 is provided with a radially directed toothed member 54. A second end of the clicker 50 is provided with a series of circumferentially directed saw teeth 56 (FIG. 7). Each saw tooth comprises a longitudinally directed surface and an inclined surface.

A spring member (not shown) may be provided which assists in the resetting of the clutch 60 following dispense.

Figure 8:
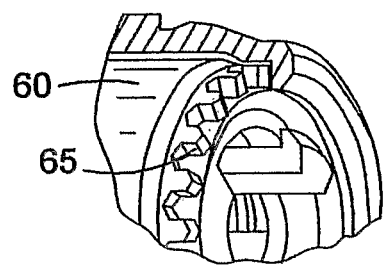
FIG. 8 shows a partially cut-away view of a third detail of the drug delivery device of FIG. 1.

The clutch 60 is located adjacent the second end of the drive sleeve 30. The clutch 60 is generally cylindrical and is provided at a first end with a series of circumferentially directed saw teeth 66 (FIG. 7). Each saw tooth comprises a longitudinally directed surface and an inclined surface. Towards the second end 64 of the clutch 60 there is located a radially inwardly directed flange 62. The flange 62 of the clutch 60 is disposed between the shoulder 37 of the drive sleeve 30 and the radially outwardly directed flange 39 of the extension 38. The second end of the clutch 60 is provided with a plurality of dog teeth 65 (FIG. 8). The clutch 60 is keyed to the drive sleeve 30 by way of splines (not shown) to prevent relative rotation between the clutch 60 and the drive sleeve 30.

In the illustrated embodiment, the clicker 50 and the clutch 60 each extend approximately half the length of the drive sleeve 30. However, it will be understood that other arrangements regarding the relative lengths of these parts are possible.

The clicker 50 and the clutch 60 are engaged as shown in FIG. 7.

A dose dial sleeve or dose setting member 70 is provided outside of the clicker 50 and clutch 60 and radially inward of the main housing 4. A helical groove 74 is provided about an outer surface of the dose dial sleeve 70.

Figure 15:
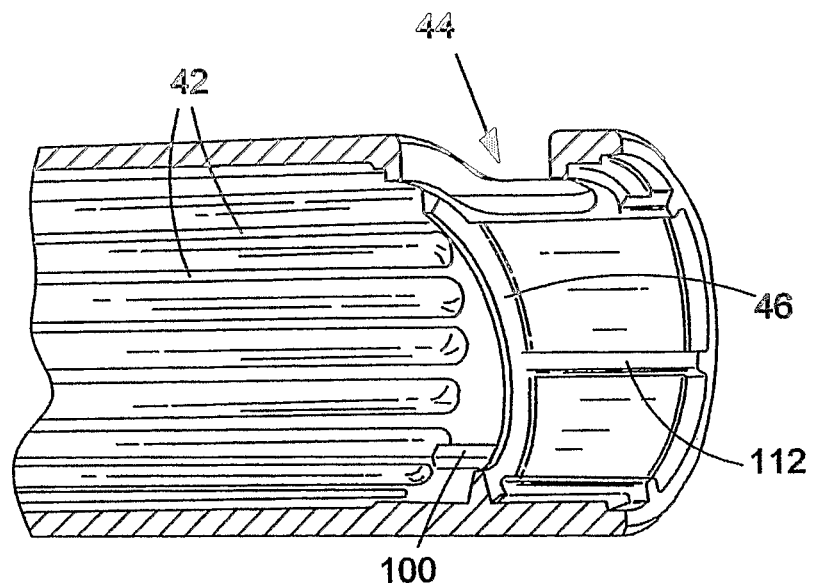
FIG. 15 shows a cut-away view of a first part of a main housing of the drug delivery device of FIG. 1.
Figure 16:
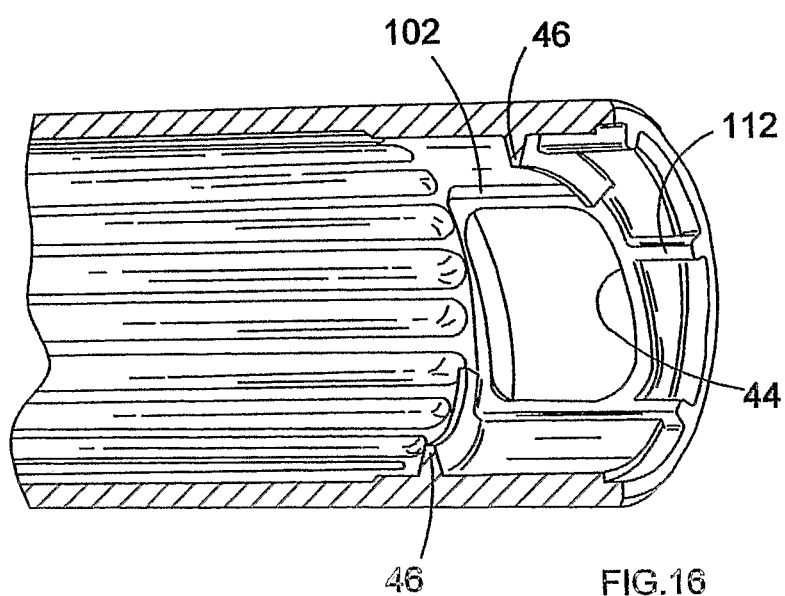
FIG. 16 shows a cut-away view of a second part of the main housing of the drug delivery device of FIG. 1.

The main housing 4 is provided with a window 44 through which a part of the outer surface of the dose dial sleeve may be seen. The main housing 4 is further provided with a helical rib (thread) 46, adapted to be seated in the helical groove (thread) 74 on the outer surface of the dose dial sleeve 70. The helical rib 46 extends for a single sweep of the inner surface of the main housing 4. A first stop 100 is provided between the splines 42 and the helical rib 46 (FIG. 15). A second stop 102, disposed at an angle of 180 degrees to the first stop 100 is formed by a frame surrounding the window 44 in the main housing 4 (FIG. 16).

Conveniently, a visual indication of the dose that may be dialed, for example reference numerals (not shown), is provided on the outer surface of the dose dial sleeve 70. The window 44 conveniently only allows to be viewed a visual indication of the dose currently dialed.

A second end of the dose dial sleeve 70 is provided with an inwardly directed flange in the form of a number of radially extending members 75. A dose dial grip 76 is disposed about an outer surface of the second end of the dose dial sleeve 70. An outer diameter of the dose dial grip 76 preferably corresponds to the outer diameter of the main housing 4. The dose dial grip 76 is secured to the dose dial sleeve 70 to prevent relative movement therebetween. The dose dial grip 76 is provided with a central opening 78. An annular recess 80 located in the second end of the dose dial grip 76 extends around the opening 78.

A button 82 of generally 'T' section is provided at a second end of the device. A stem 84 of the button 82 may extend through the opening 78 in the dose dial grip 76, through the inner diameter of the extension 38 of the drive sleeve 30 and into the receiving recess 26 of the piston rod 20. The stem 84 is retained for limited axial movement in the drive sleeve 30 and against rotation with respect thereto. A head 85 of the button 82 is generally circular. A skirt 86 depends from a periphery of the head 85. The skirt 86 is adapted to be seated in the annular recess 80 of the dose dial grip 76.

Figure 9:
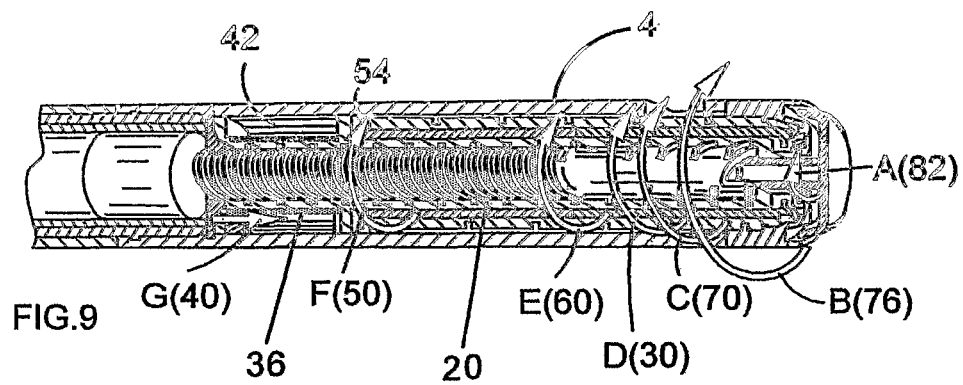
FIG. 9 shows the relative movement of parts of the drug delivery device shown in FIG. 1 during dialing up of a dose.
Figure 10:
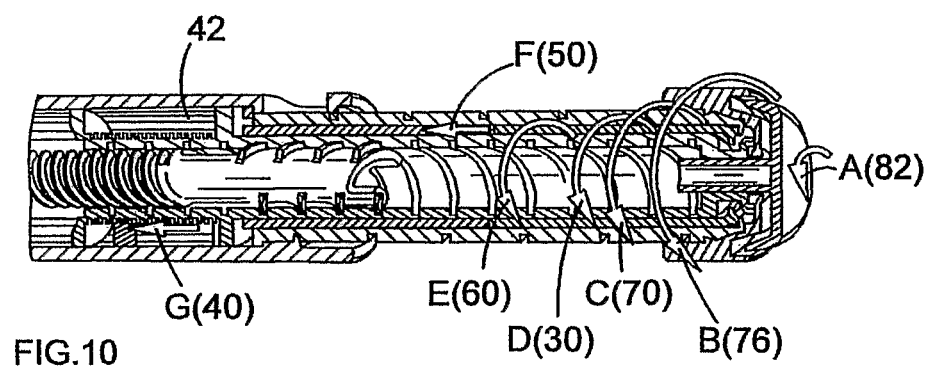
FIG. 10 shows the relative movement of parts of the drug delivery device shown in FIG. 1 during dialing down of a dose.
Figure 11:
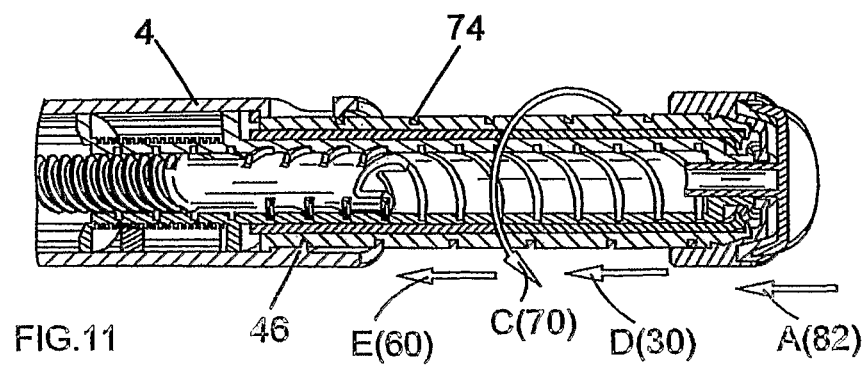
FIG. 11 shows the relative movement of parts of the drug delivery device shown in FIG. 1 during dispensing of a dose.

Operation of the drug delivery device will now be described. In FIGS. 9, 10 and 11 arrows A, B, C, D, E, F and G represent the respective movements of the button 82, the dose dial grip 76, the dose dial sleeve 70, the drive sleeve 30, the clutch 60, the clicker 50 and the nut 40.

To dial a dose (FIG. 9) a user rotates the dose dial grip 76 (arrow B). With the clicker 50 and clutch 60 engaged, the drive sleeve 30, the clicker 50, the clutch 60 and the dose dial sleeve 70 rotate with the dose dial grip 76.

Audible and tactile feedback of the dose being dialed is provided by the clicker 50 and the clutch 60. Torque is transmitted through the saw teeth 56,66 between the clicker 50 and the clutch 60. The flexible arm 52 deforms and drags the toothed member 54 over the splines 42 to produce a click. Preferably, the splines 42 are disposed such that each click corresponds to a conventional unit dose, or the like.

Figure 12:
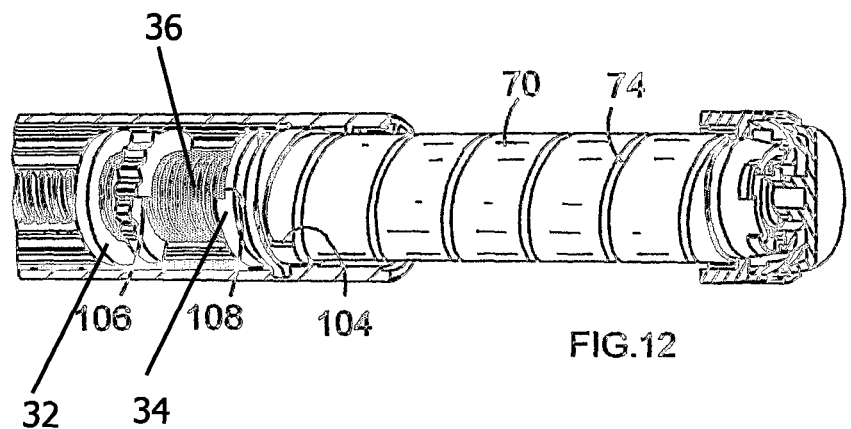
FIG. 12 shows a partially cut-away view of the drug delivery device of FIG. 1 in the second, maximum first dose dialed, position.

The helical groove 74 on the dose dial sleeve 70 and the helical groove 38 in the drive sleeve 30 have the same lead. This allows the dose dial sleeve 70 (arrow C) to extend from the main housing 4 and the drive sleeve 30 (arrow D) to climb the piston rod 20 at the same rate. At the limit of travel, a radial stop 104 (FIG. 12) on the dose dial sleeve 70 engages either the first stop 100 or the second stop 102 provided on the main housing 4 to prevent further movement. Rotation of the piston rod 20 is prevented due to the opposing directions of the overhauled and driven threads on the piston rod 20.

Figure 13:
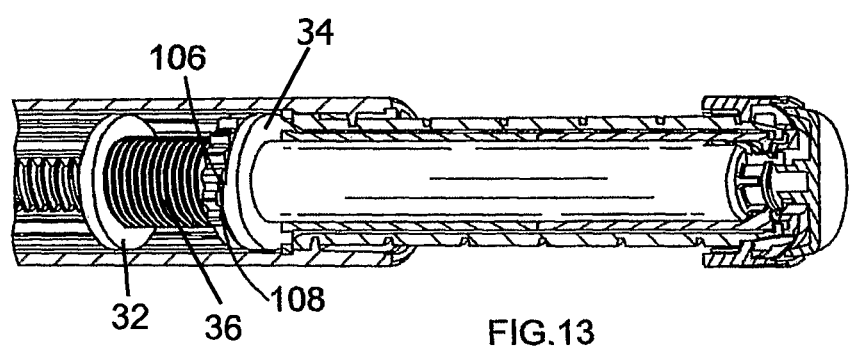
FIG. 13 shows a partially cut-away view of the drug delivery device of FIG. 1 in the fourth, final dose dialed, position.

The nut 40, keyed to the main housing 4, is advanced along the intermediate thread 36 by the rotation of the drive sleeve 30 (arrow D). When the final dose dispensed position (FIGS. 4, 5 and 13) is reached, a radial stop 106 formed on a second surface of the nut 40 abuts a radial stop 108 on a first surface of the second flange 34 of the drive sleeve 30, preventing both the nut 40 and the drive sleeve 30 from rotating further.

In an alternative embodiment (not shown) a first surface of the nut 40 is provided with a radial stop for abutment with a radial stop provided on a second surface of the first flange 32. This aids location of the nut 40 at the cartridge full position during assembly of the drug delivery device.

Should a user inadvertently dial beyond the desired dosage, the drug delivery device allows the dosage to be dialed down without dispense of medicinal product from the cartridge (FIG. 10).

The dose dial grip 76 is counter rotated (arrow B). This causes the system to act in reverse. The flexible arm 52 preventing the clicker 50 from rotating. The torque transmitted through the clutch 60 causes the saw teeth 56,66 to ride over one another to create the clicks corresponding to dialed dose reduction. Preferably the saw teeth 56,66 are so disposed that the circumferential extent of each saw tooth corresponds to a unit dose.

When the desired dose has been dialed, the user may then dispense this dose by depressing the button 82 (FIG. 11). This displaces the clutch 60 axially with respect to the dose dial sleeve 70 causing the dog teeth 65 to disengage. However the clutch 60 remains keyed in rotation to the drive sleeve 30. The dose dial sleeve 70 and associated dose dial grip 76 are now free to rotate (guided by the helical rib 46 located in helical groove 74).

The axial movement deforms the flexible arm 52 of the clicker 50 to ensure the saw teeth 56,66 cannot be overhauled during dispense. This prevents the drive sleeve 30 from rotating with respect to the main housing 4 though it is still free to move axially with respect thereto. This deformation is subsequently used to urge the clicker 50, and the clutch 60, back along the drive sleeve 30 to restore the connection between the clutch 60 and the dose dial sleeve 70 when pressure is removed from the button 82. Additionally or alternatively, the spring member (not shown) can be used to restore the connection between the clutch 60 and the dose dial sleeve 70.

Figure 14:
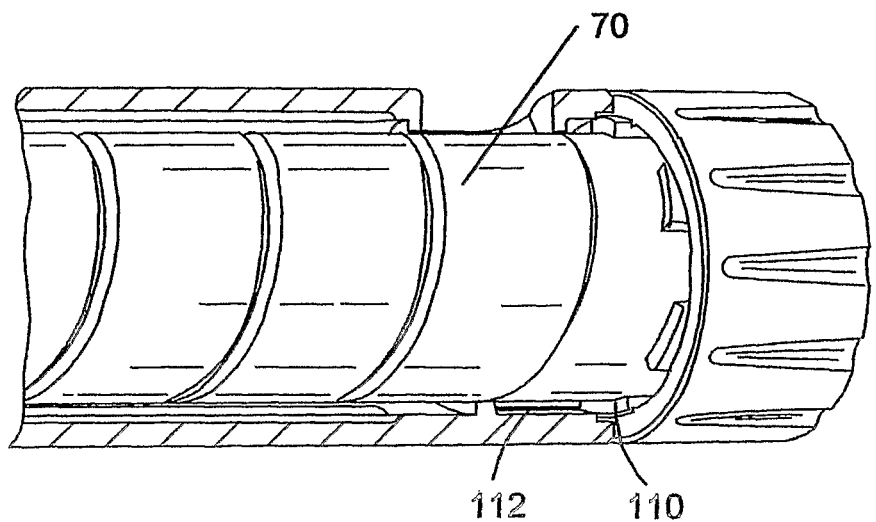
FIG. 14 shows a partially cut-away view of the drug delivery device of FIG. 1 in one of the first, third or fifth positions.

The longitudinal axial movement of the drive sleeve 30 causes the piston rod 20 to rotate though the opening 18 in the insert 16, thereby to advance the piston 10 in the cartridge 8. Once the dialed dose has been dispensed, the dose dial sleeve 70 is prevented from further rotation by contact of a plurality of members 110 (FIG. 14) extending from the dose dial grip 76 with a corresponding plurality of stops 112 formed in the main housing 4 (FIGS. 15 and 16). In the illustrated embodiment, the members 110 extend axially from the dose dial grip 76 and have an inclined end surface. The zero dose position is determined by the abutment of one of the axially extending edges of the members 110 with a corresponding stop 112.

After the dose has been delivered and the connection between the clutch 60 and the dose dial sleeve 70 has been restored, the device is ready for setting a further dose.

In the drug delivery device as described above, it has been found, when industrializing this device, that a separate spring member described above which is made from metal is necessary for a reliable operation of the drug delivery device in order to reengage the clutch 60 with the dose dial sleeve 70.

Figure 21:
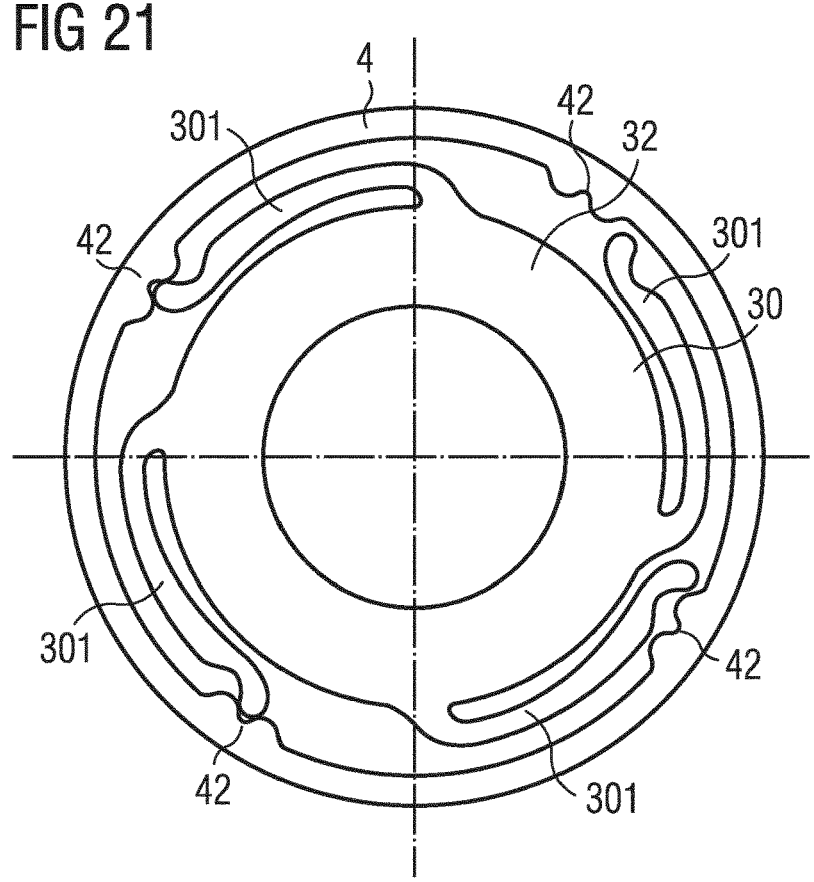
FIG. 21 shows a cut-away view of parts of an embodiment of an alternative clicker mechanism for the drug delivery device of FIGS. 1 to 16, where the cut is taken perpendicularly to a longitudinal axis of the device.
Figure 22:
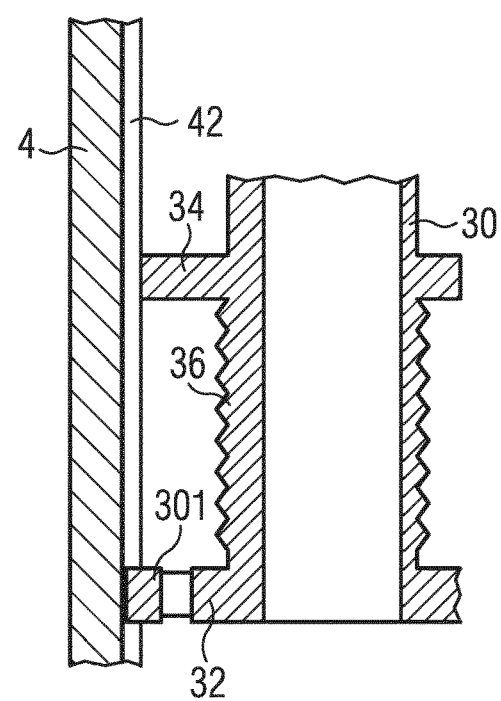
FIG. 22 shows a cut-away view of parts of an embodiment of an alternative clicker mechanism for the drug delivery device of FIGS. 1 to 16, where the cut is taken along the longitudinal axis of the device.

In the following text, a simplified mechanism for the drug delivery device of FIGS. 1 to 16 is described, which achieves the same functionality as the one described above but has a reduced part count and also enables to dispense with a separate spring member. Consequently, all features which are disclosed above for the device also apply in the following text except that certain features are altered as explained below. The mechanism described below provides a clutch functionality in order to selectivity rotationally lock the drive member or drive sleeve 30 with respect to the housing 4. FIGS. 17 to 20 illustrate such a mechanism. FIGS. 21 and 22 illustrate a clicker mechanism which may be an alternative clicker mechanism to the one described above. The clicker mechanism may be provided in addition to the clutch mechanism or just as an alternative to the clicker mechanism described above. Particularly, the clicker 60 as described above may, in addition to the spring member, be dispensed with if the mechanisms as disclosed in FIGS. 17 to 22 and described below are used in the device of FIGS. 1 to 16.

Figure 17:
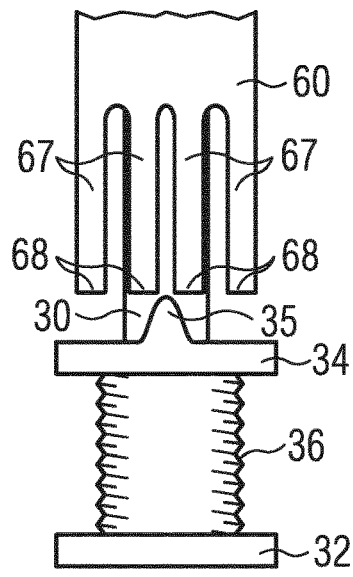
FIG. 17 shows a view of parts of an embodiment of an alternative clutch mechanism for the drug delivery device of FIGS. 1 to 17 in a first relative position.

At first, the alternative mechanism shown in FIGS. 17 to 20 is described. The main components of the mechanism are the drive member 30 and the clutch member 60 as depicted in FIG. 17. The clutch member 60 and the drive member 30 largely correspond to those described above. However, they are modified so as to provide an additional clutch functionality which is not included in the embodiment described in conjunction with FIGS. 1 to 16.

According to FIG. 17, the clutch member 60 comprises one or more deflectable features 67, which are expediently elastically deflectable. The elastically displaceable features are disposed circumferentially around the clutch member 60. Particularly, the features 67 are evenly distributed in the circumferential direction. The deflectable features 67 may define a distal end of the clutch member 60. The deflectable features 67 are unitarily formed with the clutch member 60 which may be a plastic component. The respective deflectable feature 67 extends axially. The distal direction is the downward direction in FIG. 17. The respective deflectable feature 67 is a finger, which may extend largely in the axial direction in an undeflected state as depicted in FIG. 17. The axial direction may extend along the main longitudinal axis of the device as shown in FIGS. 1 through 16. The respective deflectable feature 67 is elastically deformable or deflectable on account of the spaced deposition of the features 67 with respect to each other in the circumferential direction which provides resilience to the respective feature. The respective deflectable feature 67, as can best be seen in the sectional views in FIGS. 18 to 20, has a free end 68. The free end 68 may protrude in the radial direction from the remainder of the deflectable feature 67, particularly in an undeflected state and/or in a deflected state of the feature 67. An inner surface 69 of the deflectable feature 67 extends away from the free end 68, particularly also in the proximal direction. The elastically deflectable features 67 are radially deflectable with respect to a clutch member body which is that section of the clutch member 60 arranged subsequent to the deflectable features 67 in the proximal direction in the figures.

Furthermore, contrary to the embodiment disclosed in conjunction with FIGS. 1 to 16, the drive member 30 comprises an interaction feature 35. The interaction feature 35 is provided on a radially protruding portion 34 of the drive member 30. The radially protruding portion may be flange 34 as detailed further above. Flange 34 is provided more proximally than flange 32. The interaction feature 35 has a surface 31 which is oblique. The surface 31 is arranged to cooperate with the inner surface 69. The surface 31 is expediently an outer surface or outwardly facing surface. The interaction feature 35 is spaced in the radial direction from a main body of the drive member 30 and protrudes from the protruding portion 34 in the axial, preferably the proximal, direction. The interaction feature 35 is unitarily formed with the drive member 30 which may be a plastic component.

The deflectable feature 67, particularly its inner surface 69, is designed to interact with, e.g. to abut, the interaction feature 35, particularly the oblique surface 31, in order to displace the deflectable feature 67 and, particularly, its free end 68 in the radial direction, such as with respect to the drive member 30 and also with respect to the remainder of the clutch member 60 when the clutch member is moved distally relative to the drive member 30. The inner surface 69 of the deflectable feature 67 may have a section which is curved or oblique. The radius of curvature of the inner surface 69 may increase from an interaction section which is designed to interact with the interaction feature in the proximal direction. In other words, the radius of curvature of the inner surface 69 may be greater in a first section of the deflectable feature than in a second section which is further away from the free end 68 than the first section. The first section is preferably a section within which the deflectable features 67 cooperates with the interaction feature. In the second section, which may be further away from the free end 68 than the first section, there is preferably no mechanical cooperation of deflectable features 67 and interaction feature 35 in none of the relative positions of drive member 30 and clutch member 60. Instead of providing one interaction feature 35 as illustrated in the exemplary embodiment depicted, there is preferably one interaction feature assigned to each deflectable feature 67 or one interaction feature 35 which cooperates with a plurality of deflectable features 67 such as an interaction feature which has a ring-like shape.

The interaction feature 35 and particularly its surface 31 may be inwardly offset from an outer edge 33 of the protruding portion 34. The region between the edge 33 and the surface 31 may constitute an end stop surface which limits the relative displacability of the clutch member 60 and the drive member 30 in the axial direction. For example, when the deflectable feature hits the radial protruding portion, no further displacement may be possible.

Figure 18:
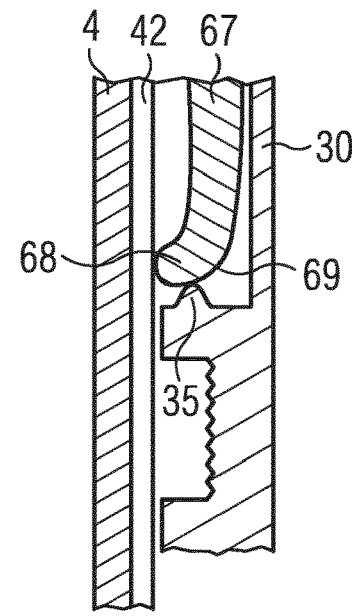
FIG. 18 shows a cut-away view of parts of the clutch mechanism of FIG. 17 for the drug delivery device in the first relative position.

FIGS. 17 and 18 show the clutch member 60 and the drive member 30 in a first relative position. In the first relative position clutch member 60 and drive member 30 are rotatable with respect to the main housing 4 as there is no interaction between the deflectable features 67 and the splines 42. In particular the deflectable feature 67, which may but need not be illustrative for a plurality of features 67, and particularly its free end 68, is not engaged with the spline 42 in the main housing 4. The splines engagable by the deflectable features 67 need not be the splines 42 described further above but could also be separate splines provided in the housing 4. However, it is advantageous to use the splines 42 for this purpose, as they are already incorporated in the main housing of the device disclosed in FIGS. 1 to 16 such that the design of the housing and also the molds to manufacture the housing need not be changed. It is preferred that, in the first relative position, as depicted in FIGS. 17 and 18, the deflectable feature 67 abuts the interaction feature 35. The clutch member and the drive member are in the first relative position during setting of the dose, for example, or when a set dose is decreased or cancelled.

Figure 19:
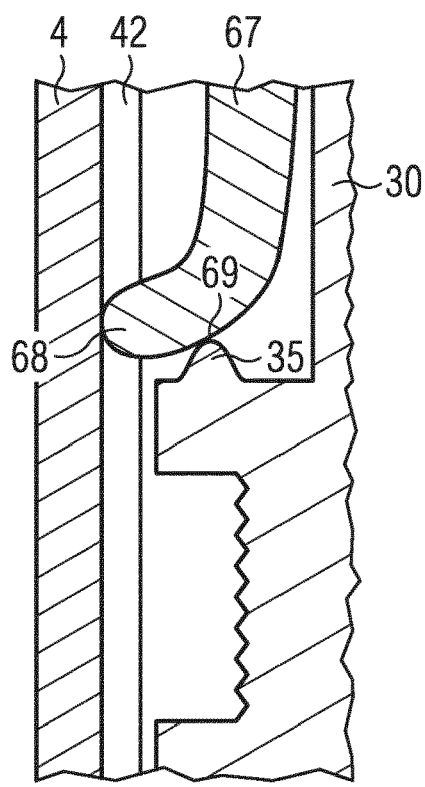
FIG. 19 shows a cut-away view of parts of the clutch mechanism of FIG. 18 in a second relative position.

When the clutch member 60 is displaced in the distal direction with respect to the drive member 30 the elastically deflectable feature 67 is deflected radially outwardly, particularly due to cooperation of the surfaces 69 and 31. This displacement is effected if the button 82 is pressed by the user to dispense a previously set dose as previously described in conjunction with FIGS. 1 to 16. When the elastically deflectable feature and particularly its free end 68 have been displaced into the second relative position as depicted in FIG. 19, for example, the elastically deflectable feature engages one of the splines 42 in the housing 4 and thus rotationally locks the clutch member 60 to the housing 4. As the drive member 30 and the clutch member 60 are splined to one another, this also rotationally locks the drive member 30 to the main housing 4. During the distal movement of the clutch member 60 with respect to the drive member 30 from the first into the second relative position, the drive member may be stationary. The distal movement of the clutch member 60 with respect to the drive member 30 may be stopped when the deflectable feature abuts an inner surface of the housing 4 and/or when the deflectable feature bears on the protruding portion 34 in the region between the edge 33 and the oblique surface 31.

The splines 42 are preferably evenly distributed in the circumferential direction. Consequently two or more deflectable features may interact with a respectively associated spline 42. This strengthens the rotational lock relative to the housing.

The axial extension of the interaction feature preferably corresponds to or is greater than the distance which the clutch member 60 has to be displaced relative to the dose setting member 70 in order to decouple the clutch 60 from the dose setting member 70.

Figure 20:
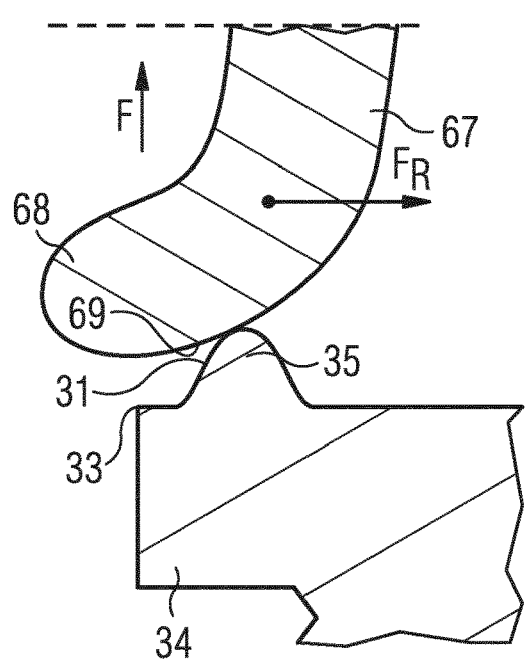
FIG. 20 shows a cut-away view of parts of the clutch mechanism in the second relative position.

When the clutch member 60 and the drive member 30 are in the second relative position as depicted in FIGS. 19 and 20, on account of the elastic deformation of the elastically deflectable features 67, e.g. from an undeformed state as depicted in FIGS. 17 and 18 to a deformed state as depicted in FIGS. 19 and 20, there is an elastic restoring force $F_R$, which tends to restore the undeformed shape of the deflectable feature and/or which tends to move the elastically deflectable feature back towards its initial position depicted in FIGS. 17 and 18. In the present embodiment, this force $F_R$ is radially and/or inwardly directed. On account of the interaction of surfaces 69 and 31, the force $F_R$ results in a force F which wants to separate the clutch member and the drive member from one another. The force F is axially, particularly proximally directed. As long as there is a force exerted by the user, such as on the button 82, e.g. to dispense a dose, the separating movement is not possible as the force F is counteracted by the user. However, when the user releases the dose button the restoring movement of the deflectable feature towards its undeflected position is possible and, while the surface 69 slides along surface 31, the clutch member 60 is moved towards the first relative position, e.g. proximally with respect to the drive member, by the force F as depicted in FIG. 20. Thereby, the deflectable features 67 are disengaged from the housing 4. Also, the clutch member 60 is reengaged with the dose dial sleeve or dose dial member 70. After the restoring movement has been completed, the assembly may again be in the first relative position depicted in FIGS. 17 and 18 and ready for setting the next dose.

Of course, the deflectable feature 67 could also be provided on the drive member 30 instead of on the clutch member 60. The interaction feature 35 would then be provided on the clutch member 60. An assembly like this would provide the same or similar functionality as the one described above.

In contrast to the embodiment disclosed in FIGS. 1 to 16, two components, i.e. clicker 50 and the spring member to reengage the clutch 60 with the dose setting member 70, can be dispensed with, if the clutch mechanism as described in conjunction with FIGS. 17 to 20 is applied. This considerably reduces the part count.

Of course, it is advantageous to provide a clicker functionality as disclosed in FIGS. 1 to 16 which provides audible and/or tactile feedback, particularly when the dose dial sleeve or dose dial member 70 is rotated relative to the housing 4 to set a dose and/or when the dose is cancelled or adjusted, such as increased further and/or decreased.

In conjunction with FIGS. 21 and 22 a mechanism is disclosed which could be implemented as a clicker mechanism in the device described in conjunction with FIGS. 1 to 16 in addition to the clutch mechanism described above in connection with FIGS. 17 to 20 or as a stand-alone solution and as an alternative to the clicker mechanism disclosed in FIGS. 1 to 16.

The clicker mechanism comprises a plurality of feedback features 301. The feedback features are provided at, preferably integrated in, the drive member 30. The feedback features are provided circumferentially around flange 32 of the drive member 30. The feedback features 301 are formed as flexible fingers which preferably extend azimuthally. The feedback features 301 are radially deformable. The feedback features 301 are unevenly distributed in the circumferential or azimuthal direction around the drive sleeve in order to guarantee that at least two feedback features 301 are engaged with corresponding features at the housing 4 (for example splines 42), which are evenly distributed in the circumferential or azimuthal direction, in each relative position which the drive member 30 assumes relative to the housing 4 for different dosage increments, for example during dose setting. In the exemplary embodiment four feedback features 301 are provided for four corresponding features. However, it is advantageous to provide more feedback features and/or more spline features. The number of corresponding features may be greater than the one of the feedback features 301, particularly if the corresponding features have an additional functionality, such as for example providing a rotational lock as outlined above with respect to the clutch mechanism. When the feedback features engage a corresponding feature and/or disengage a corresponding feature, a clicking sound may be generated.

All members disclosed in FIGS. 17 to 22 can be plastic components. Therefore, the disclosed mechanisms can be manufactured in a very cost-effective but yet reliable manner. Furthermore, by means of the clutch and clicker mechanism disclosed herein, the same functionality may be provided as in the device disclosed in FIGS. 1 to 16, but without the need of a clicker 50 and also without the need of an additional metal spring for reengaging the clutch and the dose setting member. Still further, the axial load on the feedback features can be reduced as the feedback features are not deformed axially, such as to reengage the clutch member and the dose member which is one option described in conjunction with FIGS. 1 to 16.

Although the exemplary embodiments disclosed above in conjunction with FIGS. 17 to 22 were disclosed for the drug delivery device in FIGS. 1 to 16, they could well also be applied to different drug delivery devices and have the same advantages. However, of course as the above-described drug delivery device is a disposable drug delivery device, cost-effective manufacturing is of particular importance, which is why the disclosed concepts are particularly suitable for the drug delivery device of FIGS. 1 to 16.

The scope of protection of any invention contained in this disclosure is not limited to the examples given hereinabove. Rather, the invention is embodied in each novel characteristic and each combination of characteristics, which particularly includes every combination of any features which are stated in the claims, even if this feature or this combination of features is not explicitly stated in the claims or in the examples.

LIST OF REFERENCES 2 retaining part
4 main housing
6 retaining features
8 cartridge
10 piston
12 removable cap
14 replacable cap
16 insert
18 circular opening
19 first thread
20 piston rod
22 pressure foot
24 second thread
26 receiving recess
30 drive sleeve/drive member
31 outer surface
32 first flange
33 outer edge
34 second flange
35 interaction feature
36 intermediate thread
37 shoulder
38 helical thread
39 flange
301 feedback feature
40 nut
42 splines
44 window
46 helical thread
50 clicker
52 arm
54 member
56 teeth
60 clutch/clutch member
62 flange
64 second end
65 teeth
66 teeth
67 deflectable feature
68 free end
69 inner surface
70 dose dial sleeve/dose setting member
74 helical groove
75 extending members
76 grip
78 opening
80 recess
82 button
84 stem
85 head
86 skirt
100 first stop
102 second stop
104 radial stop
106 radial stop
108 radial stop
110 members
112 stops
150 helical thread
F Force
$F_R$ Force

The invention claimed is:

1. An assembly for a drug delivery device, the assembly comprising:
a housing;
a clutch member, the clutch member being a clutch sleeve; and
a drive member, wherein the drive member is received in the clutch member, wherein:
the clutch member is provided with at least one deflectable feature, the at least one deflectable feature being an axially oriented finger arranged to be deflected radially and being provided at a distal end of the clutch member,
the drive member is provided with at least one interaction feature,
the clutch member and the drive member are movable relative to one another between a first relative position and a second relative position,
in the first relative position, the clutch member and/or the drive member is rotatable relative to the housing,
in the second relative position, the at least one deflectable feature is arranged to prevent rotation of the clutch member and/or of the drive member relative to the housing, and
the at least one deflectable feature and the at least one interaction feature are arranged such that, when the clutch member and the drive member are moved relative to one another from the first relative position into the second relative position, the at least one deflectable feature and the at least one interaction feature mechanically interact in order to deflect the at least one deflectable feature.

2. The assembly of claim 1, wherein the clutch member is splined to the drive member.

3. The assembly of claim 1, wherein the at least one deflectable feature comprises an elastically deflectable feature and wherein, in the second relative position, the elastically deflectable feature provides a force to establish the first relative position between the clutch member and the drive member.

4. The assembly of claim 1, wherein the at least one interaction feature comprises an oblique surface arranged to deflect the at least one deflectable feature in a radial direction when the at least one deflectable feature contacts the oblique surface and when the clutch member and the drive member are moved relative to one another in an axial direction from the first relative position into the second relative position.

5. The assembly of claim 1, wherein the clutch member comprises a clutch feature designed to mechanically interact with a movable member of the assembly in order to releasably couple the clutch member and the movable member rotationally.

6. The assembly of claim 1, further comprising a plurality of deflectable features evenly distributed circumferentially.

7. The assembly of claim 1, further comprising a piston rod, wherein the drive member is arranged to mechanically interact with the piston rod to drive the piston rod relative to the housing.

8. The assembly of claim 1, wherein the at least one interaction feature is arranged on a radially protruding portion of the drive member, and the at least one interaction feature protrudes axially from the radially protruding portion.

9. The assembly of claim 1, wherein the drive member or the clutch member is provided with a plurality of feedback features designed to releasably mechanically engage corresponding features on the housing to generate an audible and/or tactile feedback when the drive member and/or the clutch member rotates relative to the housing.

10. The assembly of claim 9, wherein each of the plurality of feedback features comprises a flexible finger, the flexible finger being oriented in an azimuthal direction.

11. The assembly of claim 9, wherein the corresponding features on the housing comprise at least one feature engaged by the at least one deflectable feature to form a splined connection between the at least one deflectable feature and the housing in the second relative position.

12. The assembly of claim 9, wherein the feedback features are unevenly distributed circumferentially and wherein the corresponding features are evenly distributed circumferentially.

13. The assembly of claim 1, wherein at least one of the housing, the clutch member, the at least one deflectable feature, the drive member, or the at least one interaction feature is made of plastic.

14. The assembly of claim 1, wherein the at least one deflectable feature and the at least one interaction feature abut in the second relative position and in the first relative position.

15. The assembly of claim 1, wherein the at least one deflectable feature is unitarily formed with the clutch member.

16. The assembly of claim 1, wherein:
the at least one deflectable feature extends in an axial direction in an undeflected state and is rigidly connected or integrally formed with the clutch member.

17. The assembly of claim 16, wherein the at least one deflectable feature and the interaction feature are arranged such that, when the clutch member and the drive member are moved relative to one another from the first relative position into the second relative position, the at least one deflectable feature and the interaction feature mechanically interact in order to deflect the at least one deflectable feature radially towards the housing.

18. A drug delivery device comprising:
an assembly comprising
a housing;
a clutch member, the clutch member being a clutch sleeve; and
a drive member, wherein the drive member is received in the clutch member, wherein
the clutch member is provided with at least one deflectable feature, the at least one deflectable feature being an axially oriented finger arranged to be deflected radially and being provided at a distal end of the clutch member,
the drive member is provided with at least one interaction feature,
the clutch member and the drive member are movable relative to one another between a first relative position and a second relative position,
in the first relative position, the clutch member or the drive member is rotatable relative to the housing,
in the second relative position, the at least one deflectable feature is arranged to prevent rotation of the clutch member or of the drive member relative to the housing, and
the at least one deflectable feature and the at least one interaction feature are arranged such that, when the clutch member and the drive member are moved relative to one another from the first relative position into the second relative position, the at least one deflectable feature and the at least one interaction feature mechanically interact in order to deflect the at least one deflectable feature.

19. The drug delivery device of claim 18, further comprising a medicament container disposed in the housing, the medicament container containing a medicament.

* * * * *